United States Patent [19]

Goshiki

[11] Patent Number: 5,165,975
[45] Date of Patent: Nov. 24, 1992

[54] CONTRAST MEDIUM-CONTAINING TUBE

[75] Inventor: Keigo Goshiki, Saitama, Japan

[73] Assignee: Junkosma Co., Ltd., Tokyo, Japan

[21] Appl. No.: 693,384

[22] Filed: Apr. 30, 1991

[30] Foreign Application Priority Data

May 9, 1990 [JP] Japan ................................ 2-117755

[51] Int. Cl.$^5$ ..................... A61M 25/00; A61K 49/04
[52] U.S. Cl. .................................. 428/36.4; 428/36.9;
428/323; 428/402; 428/701; 428/704; 524/430;
524/434; 524/545; 524/546; 524/590; 424/4;
424/423; 424/653; 604/280; 138/DIG. 7
[58] Field of Search ................. 428/36.4, 36.9, 402,
428/323, 701, 704; 604/280; 252/478; 138/118,
DIG. 7; 128/654–658; 424/423.4, 653;
524/430, 434, 545, 546, 590

[56] References Cited

U.S. PATENT DOCUMENTS

| | | | |
|---|---|---|---|
| 2,857,915 | 10/1958 | Sheridan | 604/280 |
| 3,529,633 | 9/1970 | Vaillancourt | 604/280 |
| 3,608,555 | 9/1971 | Greyson | 252/478 |
| 4,196,731 | 4/1980 | Laurin | 604/280 |
| 4,215,033 | 7/1980 | Bowen | 428/402 |
| 4,657,024 | 4/1987 | Coneys | 604/280 |
| 4,838,879 | 6/1989 | Tanabe | 604/280 |
| 5,085,863 | 2/1992 | Goshiki | 424/423 |

Primary Examiner—Ellis P. Robinson
Assistant Examiner—Rena Dye
Attorney, Agent, or Firm—McGlew & Tuttle

[57] ABSTRACT

A contrast medium-containing tube is provided which is a thermoplastic resin tube incorporated with a white bismuth compound composed mainly of bismuth oxide containing 70–85 wt % bismuth and having a particle diameter substantially smaller than 20 μm. This contrast medium-containing tube looks white and remains white in appearance over a long period of time. It is easy to carry out extrusion molding for producing this contrast medium-containing tube.

4 Claims, No Drawings

CONTRAST MEDIUM-CONTAINING TUBE

BACKGROUND OF THE INVENTION

1. Field of the Invention

The present invention relates to a tube incorporated with an X-ray contrast medium. This contrast medium-containing tube is useful as an indwelling needle and catheter.

2. Description of the Prior Art

There is known a tube of polymeric material (like fluoroplastics having good compatibility with living organisms) incorporated with a contrast medium such as barium sulfate and bismuth oxide. This tube is used as an indwelling needle to be pierced into and fixed to a blood vessel for transfusion, because in case the needle is broken by mistake during use, it is easy to locate a broken piece of it in the blood system by radiography owing to the contrast medium contained therein. This tube is also used as a catheter to be inserted into the human body for blood collection from the heart or injection of a medicine into the internal organs, because the contrast medium helps one to bring the catheter to a desired position by radioscopy.

The contrast medium-containing tube of this kind has been known in several types. For example, Japanese Patent Publication No. 49394/1972 discloses the one in which the contrast medium is uniformly dispersed in the tube wall; Japanese Patent Laid-open No. 119263/1981 discloses the one in which the tube wall consists of three resin layers, with the intermediate layer containing a contrast medium; and Japanese Utility Model Laid-open No. 108389/1976 discloses the one in which the contrast medium forms a continuous stripe in the longitudinal direction.

The contrast medium to be incorporated into the tube for the above-mentioned purposes is usually a bismuth compound or barium sulfate. The former produces a better effect than the latter with a smaller amount because of its higher radiopaqueness. Among bismuth compounds, bismuth oxide is the highest in bismuth content and hence the most effective in radiopaqueness. Nevertheless, it is disliked by doctors and patients more than barium sulfate because it takes on a yellow color. Moreover, tubes containing bismuth oxide cannot be distinguished from one another by coloring because of their inherent yellow color.

There are white bismuth compounds such as basic bismuth carbonate and bismuth oxychloride. However, the former has such a low decomposition point that it decomposes, evolving a gas, while the resin composition containing it is processed at a high temperature. The latter is so unstable to heat and light that it becomes discolored in brown by heat during processing and by light after processing. Consequently, they cannot be a substitute for bismuth oxide.

The present inventor carried out extensive studies on making a white contrast medium-containing tube from a resin which needs a high temperature for processing. As the result, a white heat-resistant bismuth compound was found which yields the desired product. (See U.S. application Ser. No. 510,073 filed Apr. 17, 1990, now U.S. Pat. No. 5,085,863 corresponding to Japanese patent application no. 103065/1989.) However, the continued studies revealed that the contrast medium-containing tube based on this white bismuth compound tends to yellow on exposure to light for a long period of time, even though it looks white and contains no bubbles (due to the decomposition of the white bismuth compound) in the production of the tube. In order to eliminate this disadvantage, the present inventor continued his studies, which led to the present invention.

SUMMARY OF THE INVENTION

Accordingly, it is an object of the present invention to provide a contrast medium-containing tube which looks white and remains white over a long period of time and is easy to produce.

According to the present invention, the above-mentioned objective is achieved by a contrast medium-containing tube which is a thermoplastic resin tube incorporated with a white bismuth compound (having a decomposition point of about 600° C.) composed mainly of bismuth oxide containing 70–85 wt % bismuth and having a particle diameter substantially smaller than 20 μm.

Bismuth oxide varies in color depending on the bismuth content. Pure bismuth oxide of α-crystal structure, which contains more than 89 wt % bismuth, takes on a yellow color, while less pure bismuth oxide of β-crystal structure (which contains bismuth nitrate and bismuth sulfate) takes on a white color. The white bismuth compound becomes whiter with the increasing content of bismuth nitrate and bismuth sulfate; but at the same time, it decreases in bismuth content, with a concomitant adverse effect on the ability of the resin containing it to be extruded into a tube. Interestingly, it was found that a white bismuth compound with a low bismuth content is by far superior in light resistance to that with a high bismuth content. With a view to utilizing this advantage, the present inventor investigated the cause of aggravating the moldability of the resin composition incorporated with a white bismuth compound containing less bismuth. As the result, it was found that the particle diameter of the white bismuth compound plays an important role. In other words, a white bismuth compound of low bismuth content agglomerates to form large particles in the resin melt, with the result that the resin melt decreases in flowability and the moldability is poor. It was further found that even such a white bismuth compound provides good moldability if it has a particle diameter smaller than a certain level. The present invention is based on this finding.

According to the present invention, it is necessary to use a bismuth compound containing 70–85 wt % bismuth and having a particle diameter substantially smaller than 20 μm. With a bismuth content in excess of 85 wt %, the white bismuth compound is poor in light resistance. With a bismuth content less than 70 wt %, the white bismuth compound is poor in radiopaqueness.

DETAILED DESCRIPTION OF THE PREFERRED EMBODIMENT

The invention will be described in more detail with reference to the following examples which are not intended to restrict the scope of the invention.

EXAMPLES 1 TO 5 AND COMPARATIVE EXAMPLES 1 TO 3

A contrast medium with a bismuth content and particle diameter as shown in Table 1 was prepared from bismuth oxide, bismuth nitrate, and bismuth sulfate mixed together. A resin composition was prepared from 15 parts by weight of the contrast medium and 85 parts by weight of ethylene-tetrafluoroethylene (ETFE) copolymer resin. The resin composition was made into a tube by extrusion after thorough mixing. The tube was examined for appearance (color) and change in appearance (color) that occurred after exposure to the sunlight for 1 day. The results are shown in Table 1, together with the moldability of the resin composition. Moldability was rated as good if the molded tube has a smooth surface and was rated as poor if the molded tube has a rough surface.

TABLE 1

| Items | Example | | | | | Comparative Example | | |
|---|---|---|---|---|---|---|---|---|
| | 1 | 2 | 3 | 4 | 5 | 1 | 2 | 3 |
| Bismuth content (%) | 70 | 70 | 75 | 80 | 85 | 70 | 80 | 87 |
| Particle diameter ($\mu$m) | 1 | 1.5 | 10 | 5 | 20 | 25 | 25 | 25 |
| Appearance | | | | | | | | |
| Before exposure | white | white | white | white | white | white | white | white |
| After exposure | white | white | white | white | white | white | white | yellow |
| Moldability | good | good | good | good | good | poor | poor | good |

It is noted from Table 1 that the white bismuth compound as specified above i.e. with a particle diameter of at most about 20 $\mu$m, contributes to not only the production of a tube having greatly improved light resistance and color fastness but also the improvement of moldability.

The same experiment as mentioned above was repeated, with the ETFE resin (as the tube base material) replaced by other fluoroplastic resin such as tetrafluoroethylenehexafluoropropylene copolymer resin, tetrafluoroethyleneperfluoroalkylvinylether copolymer resin, tetrafluoroethylene resin, and vinylidene fluoride resin. It gave as good results as mentioned above. Needless to say, it is possible to replace the fluoroplastic resins by other thermoplastic resins such as polyurethane.

The amount of the contrast medium in the tube may vary depending on the object of the tube and the composition of the contrast medium; but it usually ranges from 3 to 25 wt % of the resin.

The contrast medium may undergo surface treatment with a coupling agent or surfactant before incorporation into the resin in order to achieve better dispersion and faster extrusion. Moreover, it may be used in combination with a proper pigment.

As mentioned above, the present invention provides a thermoplastic resin tube containing as a contrast medium a white bismuth compound prepared so as to contain 70–85 wt % bismuth and have a particle diameter substantially smaller than 20 $\mu$m. The contrast medium-containing tube is easy to make by extrusion molding and keeps its white appearance for a long period of time.

Although the invention has been described in its preferred form (with the contrast medium uniformly dispersed in the tube wall), it may be embodied in other several forms without departing from the spirit of essential characteristics thereof. For example, the contrast medium may exist in a longitudinal stripe in the tube wall or in an intermediate layer of the three-layered tube wall.

What is claimed is:

1. Contrast medium-containing tube comprising a thermoplastic resin tube having incorporated therein, as contrast medium, a white beta crystalline bismuth compound consisting essentially of bismuth oxide, bismuth nitrate and bismuth sulfate, and containing 70–85% by weight bismuth and having a particle diameter of at most about 20 $\mu$m, the tube containing 3–25% by weight of said contrast medium.

2. Tube of claim 1 wherein the tube has been formed by molding a mixture of the thermoplastic resin and said contrast medium.

3. Tube of claim 2 wherein the thermoplastic resin is fluoroplastic resin or polyurethane resin.

4. Tube of claim 1 wherein the thermoplastic resin is fluoroplastic resin or polyurethane resin.

* * * * *

UNITED STATES PATENT AND TRADEMARK OFFICE
CERTIFICATE OF CORRECTION

PATENT NO. : 5,165,975
DATED : November 24, 1992
INVENTOR(S) : Keigo Goshiki It is certified that error appears in the above-identified patent and that said Letters Patent is hereby corrected as shown below:

On the title page, the Assignee should read as follows:

[ 73 ] Assignee: Junkosha Co., Ltd., Tokyo, Japan

Signed and Sealed this

Twenty-third Day of November, 1993

Attest:

BRUCE LEHMAN

Attesting Officer    Commissioner of Patents and Trademarks